(12) United States Patent
Will et al.

(10) Patent No.: US 11,998,458 B2
(45) Date of Patent: *Jun. 4, 2024

(54) ORTHOTIC OR PROSTHETIC JOINT DEVICE, AND METHOD FOR CONTROLLING SAME

(71) Applicant: OTTOBOCK SE & CO. KGAA, Duderstadt (DE)

(72) Inventors: Christian Will, Gottingen (DE); Matthias Preis, Gernrode (DE); Sven Zarling, Duderstadt (DE); Cornelia Hartmann, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 111 days.

This patent is subject to a terminal disclaimer.

(21) Appl. No.: 17/409,659

(22) Filed: Aug. 23, 2021

(65) Prior Publication Data

US 2022/0104953 A1 Apr. 7, 2022

Related U.S. Application Data

(63) Continuation of application No. 14/412,422, filed as application No. PCT/EP2013/001868 on Jun. 26, 2013, now Pat. No. 11,096,804.

(30) Foreign Application Priority Data

Jul. 3, 2012 (DE) .......................... 102012013141.0

(51) Int. Cl.
*A61F 2/70* (2006.01)
*A61F 2/64* (2006.01)
(Continued)

(52) U.S. Cl.
CPC .................. *A61F 2/70* (2013.01); *A61F 2/64* (2013.01); *A61F 2/68* (2013.01); *A61F 5/0123* (2013.01);
(Continued)

(58) Field of Classification Search
CPC ...... A61F 2/64; A61F 2/68; A61F 2/70; A61F 2/76; A61F 5/0106; A61F 5/0123;
(Continued)

(56) References Cited

U.S. PATENT DOCUMENTS 4,608,054 A  8/1986 Schroeder
7,190,141 B1  3/2007 Ashrafiuon et al.
(Continued)

FOREIGN PATENT DOCUMENTS

DE  102008045113 A1  3/2010
DE  102009056074 A1  7/2011
(Continued)

OTHER PUBLICATIONS

PCT International Search Report for PCT International Patent Application No. PCT/EP2013/001868, dated Feb. 6, 2014.

*Primary Examiner* — Christie Bahena
(74) *Attorney, Agent, or Firm* — HOLLAND & HART LLP

(57) ABSTRACT

The invention relates to an orthotic or prosthetic joint device with an upper part and a lower part arranged in a hinged manner and fastening means for securing the joint device on a user, with at least one hydraulics unit between the upper part and the lower part, which hydraulics unit has a piston that is movable in a housing with an extension chamber and a flexion chamber and that is coupled to the upper part or the lower part, and which hydraulics unit is assigned a pressure supply device with a pump and a pressure accumulator via which the piston, controlled by a control device, is subjected
(Continued)

to a pressure, wherein the pump can be operated in generator mode, the pressure accumulator can be coupled drivingly to the pump, and the hydraulic fluid can be conveyed by the pressure accumulator through the pump to the hydraulics unit.

20 Claims, 14 Drawing Sheets

(51) Int. Cl.
| | | |
|---|---|---|
| | *A61F 2/68* | (2006.01) |
| | *A61F 5/01* | (2006.01) |
| | *A61H 1/02* | (2006.01) |
| | *A61H 3/00* | (2006.01) |
| | *A61F 2/74* | (2006.01) |
| | *A61F 2/76* | (2006.01) |

(52) U.S. Cl.
CPC ............... *A61H 1/024* (2013.01); *A61H 3/00* (2013.01); *A61F 2002/704* (2013.01); *A61F 2002/708* (2013.01); *A61F 2/74* (2021.08); *A61F 2/741* (2021.08); *A61F 2/748* (2021.08); *A61F 2002/7625* (2013.01); *A61F 2002/7635* (2013.01); *A61F 2002/7645* (2013.01); *A61F 2002/7655* (2013.01); *A61H 2003/001* (2013.01); *A61H 2201/1246* (2013.01); *A61H 2201/5061* (2013.01); *A61H 2201/5069* (2013.01); *A61H 2201/5079* (2013.01)

(58) Field of Classification Search
CPC ...... A61F 2005/0169; A61F 2002/5006; A61F 2002/745; B25J 9/00
See application file for complete search history.

(56) References Cited

U.S. PATENT DOCUMENTS

| | | | |
|---|---|---|---|
| 2001/0029343 A1 | 10/2001 | Seto et al. | |
| 2002/0152750 A1 | 10/2002 | Asai et al. | |
| 2006/0173552 A1* | 8/2006 | Roy | ............ A61F 2/64 |
| | | | 623/44 |
| 2007/0050044 A1 | 3/2007 | Haynes et al. | |
| 2007/0198098 A1 | 8/2007 | Roston et al. | |
| 2007/0233279 A1 | 10/2007 | Kazerooni et al. | |
| 2008/0022672 A1 | 1/2008 | He | |
| 2009/0299480 A1 | 12/2009 | Gilbert et al. | |
| 2010/0023133 A1 | 1/2010 | Fairbanks et al. | |
| 2010/0305716 A1 | 12/2010 | Pusch et al. | |
| 2010/0312363 A1 | 12/2010 | Herr et al. | |
| 2011/0098828 A1 | 4/2011 | Balboni et al. | |
| 2016/0030201 A1 | 2/2016 | Zoss et al. | |

FOREIGN PATENT DOCUMENTS

| | | |
|---|---|---|
| WO | 2004/017872 A1 | 3/2004 |
| WO | 2004/039292 A2 | 5/2004 |
| WO | 2006/112774 A1 | 10/2006 |
| WO | 2008/031220 A1 | 3/2008 |
| WO | 2010/088616 A1 | 8/2010 |

* cited by examiner

ORTHOTIC OR PROSTHETIC JOINT DEVICE, AND METHOD FOR CONTROLLING SAME

CROSS REFERENCE TO RELATED APPLICATIONS

This application is a continuation of U.S. patent application Ser. No. 14/412,422, filed Dec. 31, 2014, and entitled "ORTHOTIC OR PROSTHETIC JOINT DEVICE, AND METHOD FOR CONTROLLING SAME'", issued as U.S. Pat. No. 11,096,804, which is a U.S. National Entry and claims priority to PCT International Patent Application No. PCT/EP2013/001868, filed Jun. 26, 2013, and entitled "ORTHOTIC OR PROSTHETIC JOINT DEVICE, AND METHOD FOR CONTROLLING SAME", which claims priority to German Patent Application No. 102012013141, filed Jul. 3, 2012, the entire disclosures of which are incorporated herein by this reference.

TECHNICAL FIELD

The invention relates to an orthotic or prosthetic joint device with an upper part and a lower part, arranged in an articulated manner thereon, and also fastening devices for securing the joint devices on a user, with at least one hydraulic unit between the upper part and the lower part; the hydraulic unit has a piston, which is located in a housing and is coupled to the upper part or the lower part; the hydraulic unit is assigned a pressure providing device, by way of which a pressure is applied to the piston; and also a method for controlling an orthotic or prosthetic joint device.

BACKGROUND

The aim of orthotic or prosthetic devices is to compensate for disabilities in the apparatus of locomotion. In the case of patients that require orthotic or prosthetic joint devices on a lower extremity, increased concentrational effort and increased expenditure of energy is necessary, since, during walking, not only the possibly still present limbs but also the prosthetic device or orthotic device has to be accelerated, that is to say has to be moved from a rest position in a forward direction, and decelerated before setting down. In order to produce a gait that is as natural as possible, dampers are provided in prosthetic devices, assuming various tasks. Apart from standing phase damping, which provides increased stability of the prosthetic joint during the standing phase, swinging phase damping is provided, which avoids swinging into the limit stop without deceleration. The kinetic energy is converted into heat by the damper.

Furthermore, driven prosthetic devices, which actively assist pivoting of the lower part in relation to the upper part, are known from the prior art.

WO 2004/017872 A1 describes a driven prosthesis with a prosthetic knee joint that is assigned a damping unit. Likewise provided is a linear actuator, which pivots the lower leg shank with respect to the upper part. The energy is supplied by way of a flexible battery belt. The linear motor and the damper are structurally separate from one another.

WO 2006/112774 A1 relates to a combination of an actuated leg prosthesis and a passive leg prosthesis and also a method for executing a movement with a corresponding prosthesis system. The prosthesis system has a movable joint and a pump, which by way of a valve device can move a hydraulic piston in one direction or the other, so that a flexion movement or extension movement of the prosthetic knee joint is executed. The pump must produce the entire working pressure for the movement. This requires a great pump output, which in turn requires large pumps, which have a large overall volume and require correspondingly large energy storage devices.

SUMMARY

The object of the present invention is to provide an orthotic or prosthetic joint device and a method for controlling the same, which device makes energy-saving operation possible, and consequently a long time in use with comfortable control, in spite of having a high performance capability.

This object is achieved according to the invention by a device with the features of the main claim and a method with the features of the alternative independent claim. Advantageous configurations and developments of the invention are presented in the subclaims, the description and the figures.

The orthotic or prosthetic joint device with an upper part and a lower part, arranged in an articulated manner thereon, and fastening devices for securing the joint device in a user, with at least one hydraulic unit between the upper part and the lower part, which hydraulic unit has a piston, which is movable in a housing and is coupled to the upper part or the lower part and is assigned a pressure providing device with a pump and a pressure accumulator, by way of which a pressure is applied to the piston while being controlled by a control device, provides that the pressure accumulator can be coupled to the pump in a driving way. From the pressure accumulator, driving fluid can consequently be fed to the pump. The operating mode of the pump is in this case controlled by way of the pressures present and required, which are present at the hydraulic unit and the pressure accumulator. How high the respectively required pressure or volumetric flow is, and when which pressure must be present, is controlled by way of sensors, which detect loads, movement variables and/or positions, in particular angular positions. As a result, the development of pressure can be influenced by way of the pump.

The pump may be operable in generator mode, so that electrical energy can be generated when there is a surplus of mechanical or kinetic energy, for example when going down an incline.

A development provides that the hydraulic fluid can be fed from the pressure accumulator through the pump to the hydraulic unit. The possible feeding of the hydraulic fluid from the pressure accumulator through the pump to the hydraulic unit makes it possible to influence the flow of the hydraulic fluid and, in the case of a pressure of the pressure accumulator that is too high, bring about a limitation of the pressure by switching over to generator mode.

The hydraulic fluid from the pressure accumulator can be admitted to both the flexion chamber and the extension chamber, so that the control of the joint device can take place in all movement situations. Assisting the flexion and extension is possible, and similarly the deceleration of movements or the application of counterforces that go beyond an increase in damping is possible. It has been found that, for controlling orthotic or prosthetic joint devices, relatively large amounts of hydraulic fluid have to be provided relatively quickly in order to achieve timely actuation of the respective component. Those phases in which a supply of energy or a conversion of energy takes place in the case of a movement are relatively short, but an impulse-like admission of fluid with a pressure component is sometimes undesired, so that the impulse has to be attenuated or the impulse characteristic has to be adapted to the respective movement. This may take place by the feeding of the fluid through the pump, which can act as a throttle, the energy allowing itself to be converted into electrical energy by the generator mode when there is a decrease in the pressure. Nevertheless, large amounts of pressure fluid can be provided for a short time by the pressure accumulator, in order to ensure precise control and that the pressure fluid is applied to either the extension side or the flexion side of the piston. The pump is arranged downstream of the pressure accumulator, in order to assist or control the pressure accumulator.

In the pressure providing device, the pump may be coupled to the pressure accumulator or the pressure accumulators in such a way that the pressure accumulator or the pressure accumulators can be filled by way of the pump. As a result, it is possible that the pump does not have to provide the full performance capability that is necessary for moving the piston, but rather the pump can fill the pressure accumulator or the pressure accumulators continuously, so that a small, lightweight pump that operates for a longer time period can be installed. In addition, the pump is used for driving the hydraulic unit, and can be used either separately or in conjunction with the pressure accumulator or the pressure accumulators for driving the hydraulic unit.

The pressure accumulator may be coupled to the hydraulic unit exclusively by way of the pump, so that the hydraulic fluid always has to pass the pump in order to drive or decelerate the piston. As a result, the pressure of the hydraulic fluid delivered by the pressure accumulator can be varied, so that either a pressure increase or a pressure decrease can take place in the pump in order to bring the hydraulic fluid that is delivered by the pump to the hydraulic unit to the required pressure level.

Should it be necessary for pressure to be admitted suddenly to one of the chambers or both chambers, for example in a situation involving a fall or a failure of the pump, direct coupling of the chambers by way of a bypass line, with possibly interconnected valves or throttles, may be provided in order to avoid feedthrough losses and in order to be able to transport the hydraulic fluid more quickly to the chambers.

A variant of the invention provides that the pressure accumulator or the pressure accumulators is/are coupled to the flexion chamber and/or the extension chamber, so that hydraulic fluid passes from the extension chamber or flexion chamber into the pressure accumulator, so that, when there are decelerating movements, for example when going down stairs or when going down an incline on a slope, pressurized hydraulic fluid is pumped into the pressure accumulator from the corresponding chamber, so that the pressure accumulator can be filled not only by the pump, but also by way of the hydraulic piston itself. The feedthrough to the pressure accumulator may take place by way of the pump, so that, when there is a sufficient pressure level in the pressure accumulator, the pump can be operated in generator mode and used for generating power.

The pressure accumulator may be assigned a valve unit, by way of which the hydraulic fluid is introduced into the pressure accumulator or removed from it in a metered and controlled manner. As a result, the kinetic energy can be stored in the form of hydraulic pressure in the pressure accumulator and fed back to the system in a controlled manner.

The joint device may likewise be assigned a device for detecting the absolute angle, joint angle, the axial force acting on the upper part or lower part, the joint moment and/or the moments of the switching device acting on a distal connection component, so that a control in the sense of whether admission of pressure to the extension chamber or to the flexion chamber should take place can take place while taking into account the joint angle, the absolute angle, the effective axial force or the moments acting on the joint device or the connection parts to the joint device.

The pump may have a variable delivery volume, which can be adapted to the pressure in the pressure accumulator, in order that the delivery volume can be adapted to the respective fluid requirement. If the pressure in the pressure accumulator rises or falls, this can be compensated by a reduced or increased delivery volume. If only a low pressure is available in the pressure accumulator, this can be compensated by an increased delivery volume in the direction of the hydraulic cylinder. In order to be able also to increase the pressure when discharging from the accumulator, the pump may be designed as a pressure increasing pump. It may likewise be provided that the pump is designed for being operated in a generator mode, in order that the kinetic energy that cannot be converted directly as a pressure increase in the pressure accumulator is used. In this way, the pressure in the pressure accumulator can be much higher than is required in the hydraulic cylinder. When going down stairs, more energy occurs than would have to be supplied, so that the kinetic energy can be converted directly into electrical energy. Alternatively or in addition, the pressure accumulator may be operated for a short time with a very high excess pressure, which is then reduced at a suitable point in time, and possibly likewise converted into electrical energy.

The joint device is preferably designed as a prosthetic knee joint or an orthotic knee joint, but there are also other possibilities for use, for example to do with an ankle joint or a foot joint, a hip joint or to do with prostheses or orthoses on upper extremities.

The hydraulic unit may be designed as rotary hydraulics or as piston hydraulics, with a linear displacement movement.

A development of the invention provides that there are multiple pressure accumulators, which provide different pressure volumes and/or pressure levels. Different walking situations require different types of assistance. For example, when walking on the level, generally only a small impulse or minor assistance is required in the case of an extension or flexion, whereas when going up stairs a relatively great moment has to be provided for assisting the extension in order to achieve effective assistance. The arrangement of multiple different pressure accumulators allows the best pressure accumulator in each case to be selected for the walking situation concerned, so that less energy losses occur and the filling of the pressure accumulators can take place more quickly than if the maximum pressure and the maximum volume were always called upon.

The method for controlling an orthotic or prosthetic knee joint device with an upper part and a lower part arranged in an articulated manner thereon and fastening devices for securing the joint device on a user, and also with at least one drive, which provides that, before the bending or stretching, a bending moment or stretching moment that lies below the level that leads to bending or stretching is applied to the knee joint device.

It has surprisingly been found that considerable alleviation can be achieved for a patient if, before the actual bending of the knee joint device, a moment that assists the bending but is so small that bending does not yet take place is applied. The joint is consequently not actively bent, but rather the level of moment or level of force that is necessary to achieve bending is reduced. Control over the bending remains entirely with the patient or the user of the orthotic or prosthetic device. The bending is brought about by the patient when the leg provided with the prosthesis or orthosis is moved. It is not a purely passive joint that is operated by the actuation of the user alone, but rather a semiactive device is achieved, a device that leaves the initiating moment to the patient, facilitates the initiation itself and facilitates a bending, in that the moment to be applied for the bending is reduced by a preloading moment and, as bending commences, the moment is maintained for a defined time. The moment is taken over into the bending.

The same also applies to a stretching moment, which is applied before the introduction of a stretching movement or extension movement. For example when going up stairs, in the case of active knee joint devices a raising up of the patient is brought about by exerting a high amount of energy. It has been found that considerable alleviation is achieved for a patient already by an assisting application of stretching moments, the level of the stretching moment being below the level that is required to achieve complete raising up of a patient to a higher level or a reversal of movement in the swinging phase.

A development of the method provides that the bending moment that is applied by a pressure accumulator is reduced when the knee joint device is bent or before the knee joint device is bent, so that, after the initial bending and in the advanced gait cycle when lifting the front foot off the ground, the lower leg or the lower leg component is prevented from being bent unwantedly far in such a way as to produce an unnatural gait pattern. Reducing the bending moment directly before or after the bending of the joint device has the effect of ensuring that the bending itself is facilitated; active flexion assistance by the pressure accumulator during the bending, for example during the swinging phase, does not take place.

It is also possible to reduce the reduction of the bending moment directly before the bending of the knee joint device. Instead of a reduction to zero, the assisting bending moment may continue to exist, but also a reduced level in comparison with the maximum assisting bending moment. Whether the knee joint is bent can be ascertained by way of a sensor. It may likewise be provided that the bending moment is only reduced or switched off after a certain bending. It is thus possible for example only to switch off the bending moment when there is a bending of for example 4°, or to reduce the assisting bending moment over the increasing bending angle. The reduction may take place continuously or discontinuously. It may be provided that the reduction is reduced down to 0 for example from the beginning of the bending to a predetermined knee angle, for example of 5° or 6°.

In order not to provide a bending moment below the level of a bending over a long time period when no bending is to be expected in the normal gait cycle, that is to say during most of the time of the standing phase, it is provided according to the invention that the bending moment is only provided and applied in a limited time period before the bending, which is for example between 5% and 40%, in particular between 5% and 20%, of the duration of a gait cycle.

A development of the invention provides that a bending moment or stretching moment of a varying degree is provided in dependence on the walking situation. In particular in the case of normal walking on the level, there is a recurrent, uniform sequence of movements that has striking characteristics, on the basis of which the existence or absence of a walking situation can be detected. For example, walking on the level can be detected on the basis of a striking knee angle progression. If such a walking situation is detected, a bending moment adapted thereto can be provided. If for example going up an incline or going up stairs is detected, instead of or in addition to a bending moment, an extension moment that lies below the level of the actual raising up of the patient may be applied before the introduction of the swinging phase, in order to provide alleviation for the patient.

Furthermore, it is possible and intended that a varying bending moment is provided in dependence on the set-up of the prosthesis. In the case of a secure prosthesis set-up, it is necessary that a higher bending moment is applied for the bending of the prosthetic knee joint than in the case of a dynamic set-up. If a secure prosthesis set-up is chosen, there is for example increased stability in the prosthetic knee joint during standing, which may be pleasant for the wearer of the prosthesis. If a more secure prosthesis set-up is chosen, this can be made dynamic by an increase in the bending moment adapted thereto, which constitutes a noticeable alleviation during walking.

The bending moment or stretching moment is advantageously only applied up to a predetermined, ascertained knee angle. The knee angle is detected by a sensor; the respective moment is reduced or switched off before or after reaching the established knee angle.

After the introduction of the bending moment, passive damping may take place, in order to prevent the lower leg component from continuing the bending undamped. If at least one hydraulic unit between the upper part and the lower part is used for the drive, which hydraulic unit has a piston that is movable in a housing with an extension chamber and a flexion chamber and is coupled to the upper part or the lower part, and is assigned a pressure providing device with a pump and a pressure accumulator by way of which pressure is applied to the piston while being controlled by a control device, it is likewise possible that the pump is operated in generator mode in order to recover the consumed energy for providing the moment and store it in a pressure accumulator.

Furthermore, it is possible that the pump is operated in generator mode in order to convert kinetic energy into electrical energy, which can then be stored and used at a later point in time. Operating the pump in generator mode may also be used as a limitation of the pressure, so that the hydraulic fluid cannot get into the pressure accumulator without a reduction of the pressure. As a result, controlled filling with pressure limitation, while at the same time utilizing the entire kinetic energy, is possible when going down an incline.

A reduction of the stretching moment may be initiated before reaching the stretching limit stop, in order to prevent the lower leg from entering the stretching limit stop without being decelerated and with the assistance of the pressure providing device.

In the case of alternating climbing of stairs, the pressure providing device can apply the stretching moment in such a way that the resultant force vector is kept ahead of the pivot axis of the knee joint. The application of a stretching moment when going up stairs assists the user. It is in this case advantageous if the force vector is kept just ahead of the pivot axis or the pivot point of the knee joint, so that bending cannot take place in the stretching phase when going up stairs.

In the standing phase, the pressure providing device may actively keep the knee joint stretched by a moment, in order to prevent or hinder bending and increase the standing stability for the user.

The pressure providing device may increase the stretching moment in the initial swinging phase until the maximum bending angle is reached and maintain this until there is a reversal of movement, the bending moment being reduced again when there is a decreasing bending angle. The pressure providing device in this case acts like an extension assist spring, which counteracts a bending movement until the maximum bending angle is reached, and which releases the energy absorbed during the bending again in the stretching phase, the pressure providing device reducing the bending moment in the stretching movement as the stretching increases. Active extension assistance in the swinging phase is possible, but not necessarily provided.

Apart from a hydraulic or pneumatic drive by way of a pump, possibly with at least one pressure accumulator, a direct drive by way of an electric motor or other actuating assistance, for example a piezoelectric drive, may also be provided in order to apply a moment by which a bending or stretching of the joint device can be assisted. Applying a moment of a magnitude below an active movement has the effect that the user of the knee joint device retains full control over the initiation of the movement, the execution of the movement and the ending of the movement, which leads to greater stability during use. The energy or the moment advantageously continues to be supplied even after the beginning of the movement, in order to facilitate the execution of the movement; in this case, the energy can be supplied at an unreduced or reduced level. Before the end of the movement, the excess energy is converted by damping, in order not to execute the bending too far or not to allow the joint to enter the stretching limit stop without being decelerated in the event of stretching. The invention is advantageous in particular in the case of slow walking and in the case of prosthesis wearers with short upper leg stumps. The invention reduces the forces occurring on the shank and provides a harmonious gait pattern.

BRIEF DESCRIPTION OF THE DRAWINGS

Exemplary embodiments of the invention are explained in more detail below on the basis of the accompanying figures, in which.

DETAILED DESCRIPTION

Figure 1:
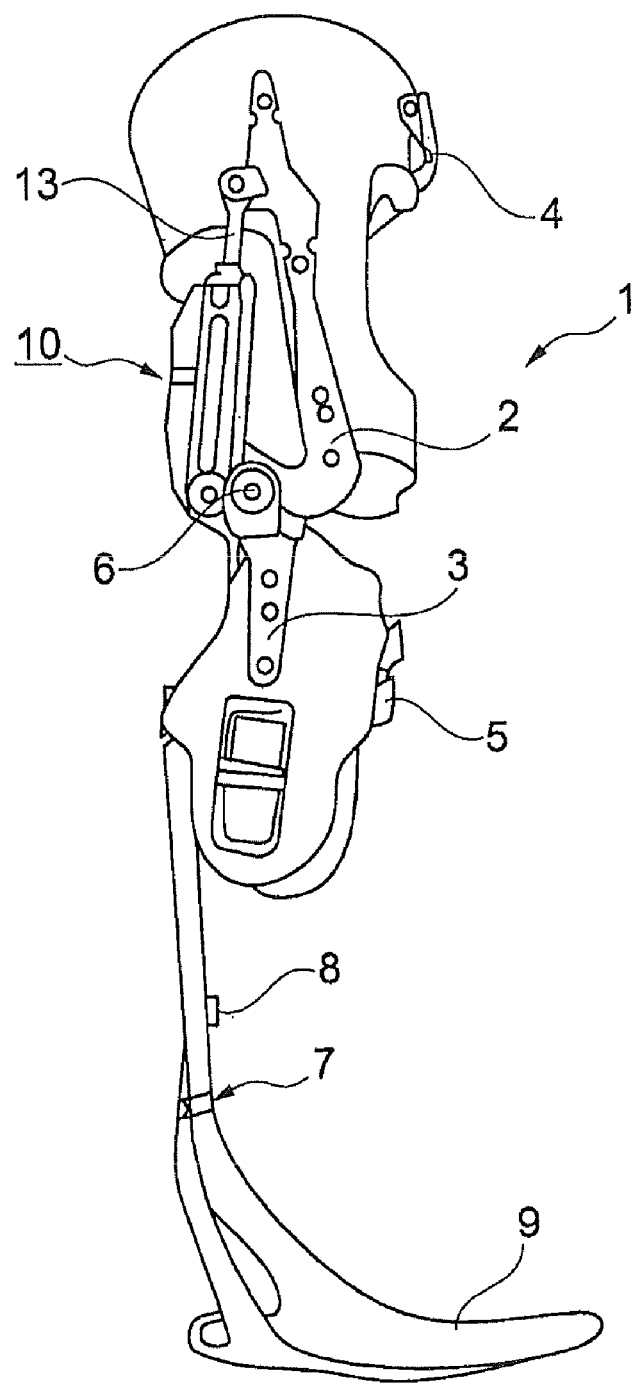
FIG. 1 shows a schematic representation of a joint device.

In FIG. 1, an orthotic joint device 1 is shown as part of a leg orthosis. The joint device 1 has an upper part 2 and a lower part arranged in an articulated manner thereon. Arranged on the upper part 2 and the lower part 3 are fastening devices 4, 5, which are formed as collars or sleeves. In the exemplary embodiment shown, the collars and sleeves are fixed to the upper leg and the lower leg of the user of the orthosis. The upper part 2 is mounted pivotably in relation to the lower part 3 about a pivot axis 6. Arranged on the lower part 3 is a foot part, on which sensors 7, 8 may be provided in order to ascertain the position of the lower part 3, the forces or moments acting thereupon or velocities. Arranged between the upper part 2 and the lower part 3 is a hydraulic unit 10, which is described in more detail below. Arranged in the hydraulic unit 10 is a piston rod 13, by way of which a displacement of the upper part 2 in relation to the lower part 3 about the pivot axis 6 is brought about. A foot part 9 is connected to the lower end of the lower part 3, in order to be able to receive a foot. Instead of an orthosis, the invention can also be realized with a prosthesis, in the case of which the fastening devices are fastened to a prosthetic sock on the upper part, while further prosthetic components, for example a lower leg shank and a prosthetic foot, are arranged on the lower part of the joint device. Corresponding arrangements may be provided and formed for joint devices on hips or upper extremities.

To assist the respective movement, that is to say the bending and stretching movement, a drive by way of which the respective movement is executed, initiated or assisted is provided in the hydraulic unit.

Figure 2:
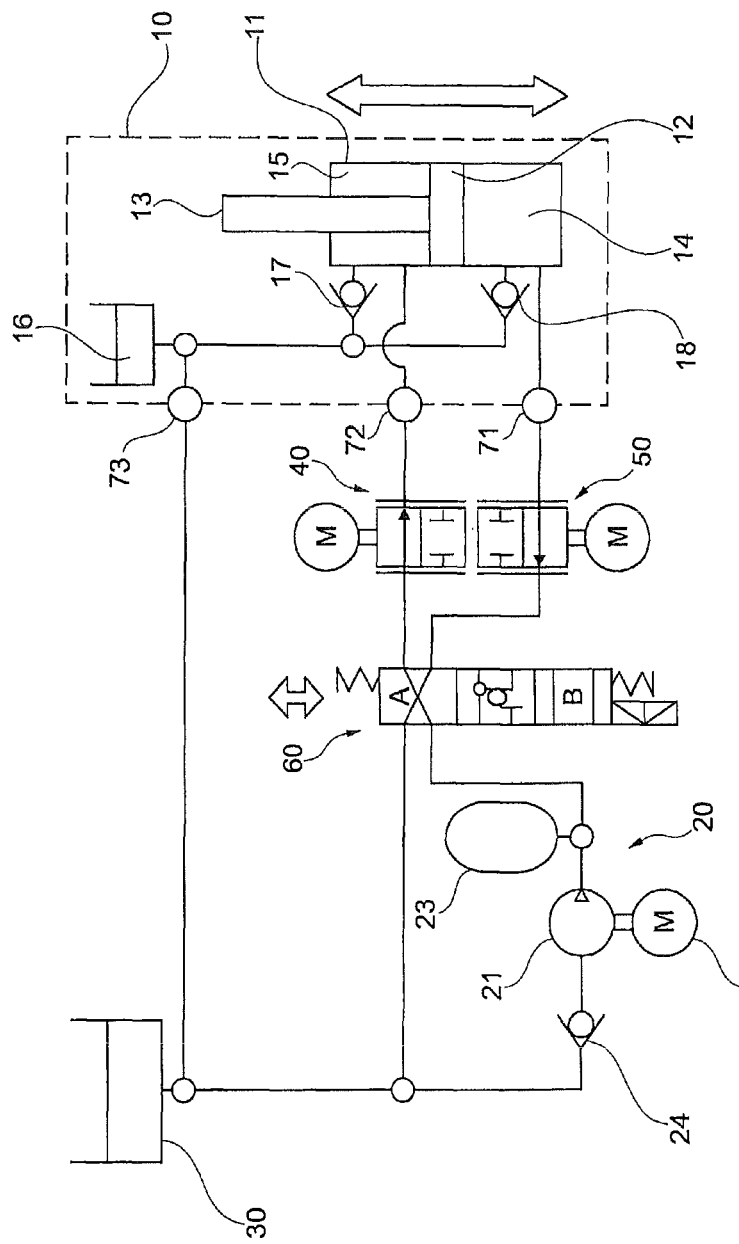
FIG. 2 shows a schematic representation of a hydraulic unit not covered by the invention.

In FIG. 2, a schematic representation of the hydraulic unit 10 with additional components is shown. The hydraulic unit 10 has a housing 11 with a piston 12, which is mounted movably thereon and is connected to the joint device by way of a piston rod 13. The housing 11 is coupled to the other component respectively of the joint device 1. In the housing 11, an extension chamber 14 is separated from a flexion chamber 15 by the piston 12. An oil reservoir 16 is connected to the extension chamber 14 and the flexion chamber 15 by way of corresponding lines and check valves 17, 18.

The hydraulic unit 10 is assigned a pressure providing device 20, by which the hydraulic system of the hydraulic unit 10 is supplied with hydraulic fluid. A hydraulic pump 21, which is driven by a motor 22, supplies the hydraulic unit 10 with pressurized hydraulic fluid. Likewise provided is a pressure accumulator 23, which likewise introduces pressurized hydraulic fluid into the hydraulic system.

The pressure providing device 20 is connected to the hydraulic unit 10 by way of a switching device 60 in the form of a switching valve. The switching device 60 of the embodiment shown can be switched into three positions, so that three different flow progressions can be realized, explained in more detail later.

Arranged between the switching device 60 and the hydraulic unit 10 are adjustable valves 40, 50, by way of which the extension damping and the flexion damping can be set. In order to drive the hydraulic unit 10, it is advisable to keep the respective dampings as small as possible, in order that less flow losses occur. The extension damping is set by way of the extension valve 40; the flexion damping is set by way of the flexion valve 50. It is possible by way of motors either to variably restrict the fluid flow or to shut it off entirely.

Pressure sensors 71, 72, 73 are provided, in order to set the valves 40, 50 in dependence on the existing pressures and the desired movements or dampings.

The switching position C shown is intended for passive movement damping, in which the pressure providing device 20 is separated from the hydraulic device 10. Extension damping and flexion damping take place by way of a setting of the respective valves 40, 50; the position of the switching device is chosen such that driving by the pressure providing device 20 is not possible. If a flexion movement is carried out, the piston 12 is forced downward. The hydraulic fluid flows through the flexion valve 50. The fluid flows out of the extension chamber 14 through the flexion valve 50 by way of the reservoir 16 back into the flexion chamber 15. On account of the reduction in the volume that can flow back, occurring due to the piston rod 13, the level in the oil reservoir 16 increases; since there is no assistance by the pump 21 or the pressure accumulator 23, this is a case of passive flexion.

Passive extension takes place in the event of a reversal of the movement, when the piston 12 moves upward and the hydraulic fluid out of the flexion chamber 15 through the extension valve 40 in the flow circuit through the switching device 60, hydraulic fluid additionally flowing into the extension chamber 14 out of the reservoir 16 of the hydraulic device 10.

Figure 3:
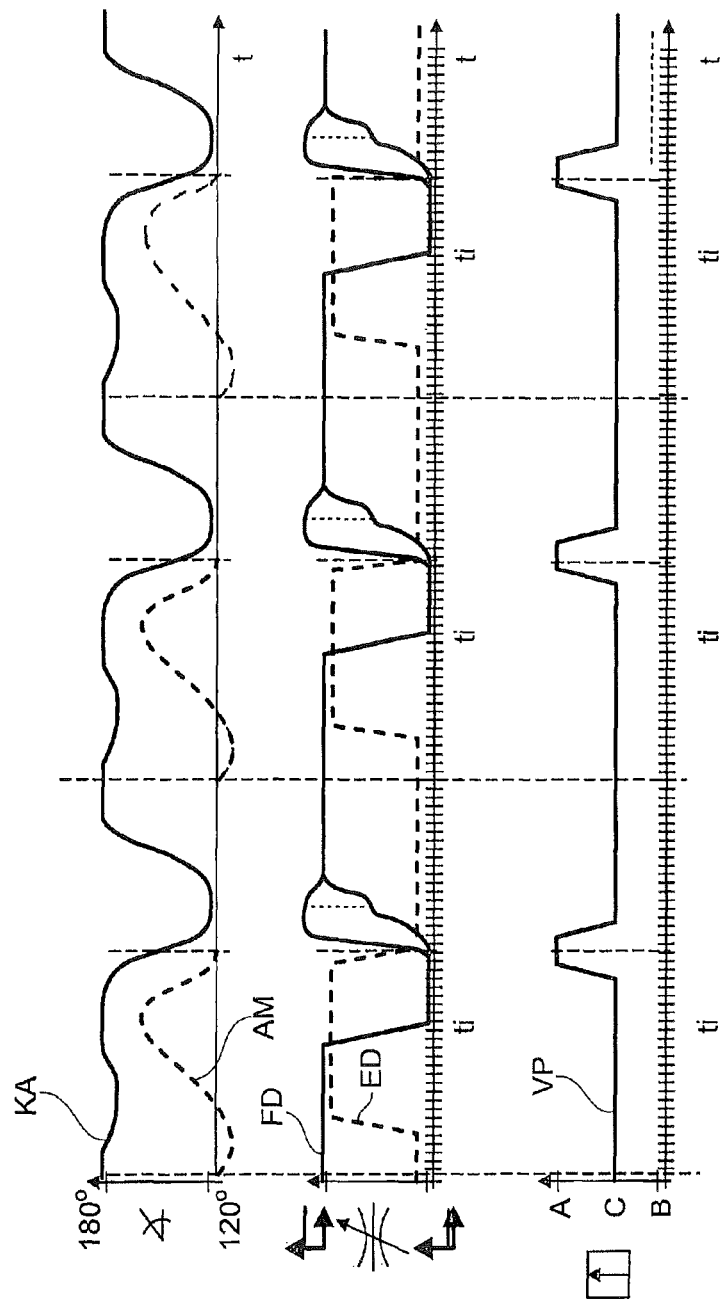
FIG. 3 shows a timing diagram for walking assistance.

In FIG. 3, three diagrams over time are shown. The upper diagram shows the knee angle KA and the ankle moment AM over time during normal walking on the level. The middle diagram shows the flexion damping FD and the extension damping ED over time during normal walking; the lower diagram shows the valve position VP at the respective point in time. The diagrams are shown for the configuration of the joint device as a prosthetic knee joint. The diagrams begin at the point in time at which the heel sets down, that is to say at the point in time of what is known as the "heel strike". The knee angle KA is 180°; the ankle moment AM acts in the direction of the plantar, and consequently runs under the horizontal line. The flexion damping FD is high, the extension damping ED low, up to the point in time at which the ankle moment AM becomes positive. Then the extension damping is raised approximately up to the level of the flexion damping FD and stays there until there is renewed forward swinging. The flexion damping FD remains high up to the point in time of the lifting off of the front foot, known as "toe off". Then the flexion damping FD is lowered, in order to make backward swinging of the lower leg possible. The flexion damping remains low until shortly before the flexion maximum, and is increased again just before reaching the flexion maximum, that is to say the lowest knee angle KA, in order on the one hand to decelerate the flexion movement and on the other hand to obtain as quickly as possible maximum security against unwanted buckling. At the same time, the extension damping ED is reduced, in order to make the most rapid possible forward movement of the lower leg and of the prosthetic foot possible. During the standing phase, the valve position VP is in the position C, in which passive flexion takes place. Shortly before the beginning of the flexion maximum, the switching device 60 is moved into the position A, in order to provide flexion assistance. The bending assistance is configured as soon as a certain knee angle is reached. Controlled extension damping ED ensures avoidance of what is known as "heel rising". The active bending assistance is detected on the basis of the progression of the ankle moment AM.

In order to ensure precise control of the hydraulic unit 10 with the valves 40, 50 and the switching device 60, sensors which monitor the individual components are provided. Apart from a knee angle sensor and an ankle moment sensor, axial force sensors may also be provided. The control may take place for example by observing the knee angle velocity. At a point of inflection of the knee angle velocity, active flexion assistance with the valve position A is activated for a certain time period. The flexion valve 50 is set to a low value and, when a defined joint angle is exceeded, the assistance is switched off and the switching device is displaced into the position C.

Figure 4:
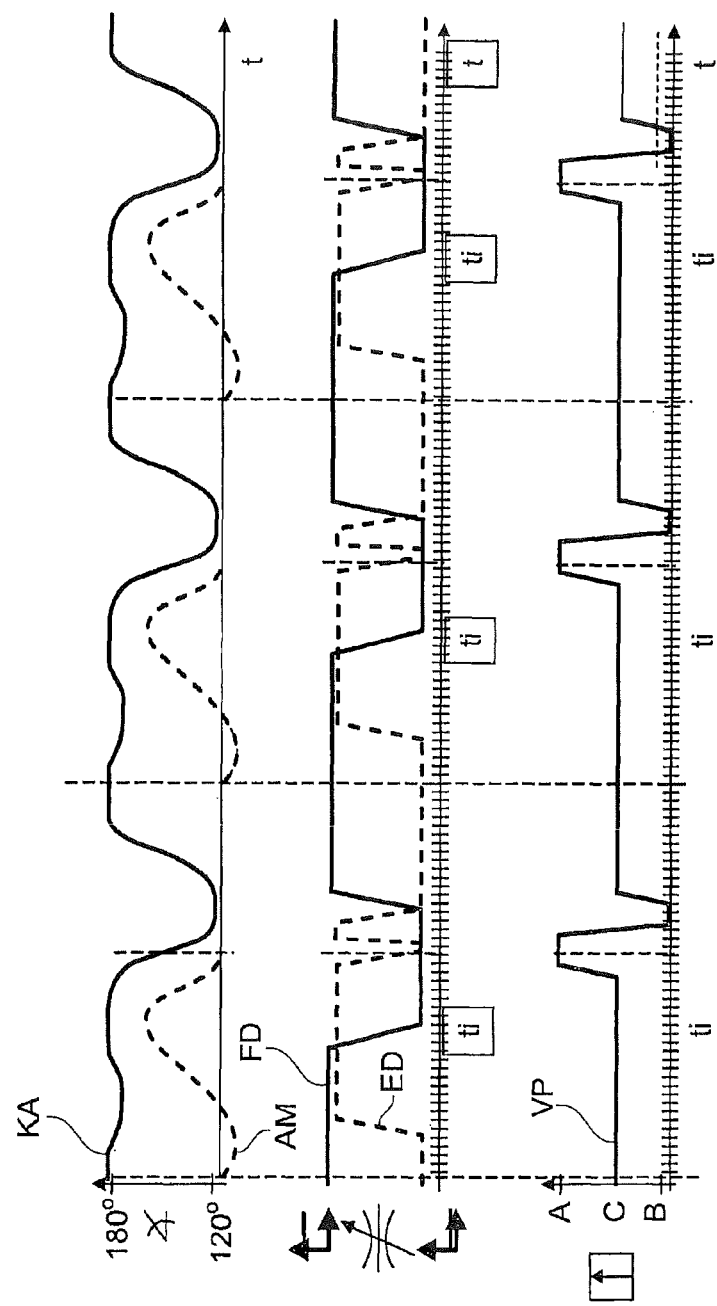
FIG. 4 shows a timing diagram for active extension assistance.

A variant of the control in which the assistance is constituted by active extension assistance is shown in FIG. 4. Until lifting off of the foot, which can be detected from the ankle moment AM, the control proceeds in the way shown in FIG. 3. Instead of again moving into the position C for the switching device 60 after the lifting off, the valve position B is assumed and the extension damping ED increased. In the valve position B of the switching device 60, the extension is assisted, that is to say that the knee angle velocity is reduced and the pivoting direction reversed. For smooth switching on of the extension assistance, the extension valve 40 may be closed and opened again at suitable points in time. Smooth switching off of the extension assistance is achieved by closing the flexion valve 50.

Figure 5:
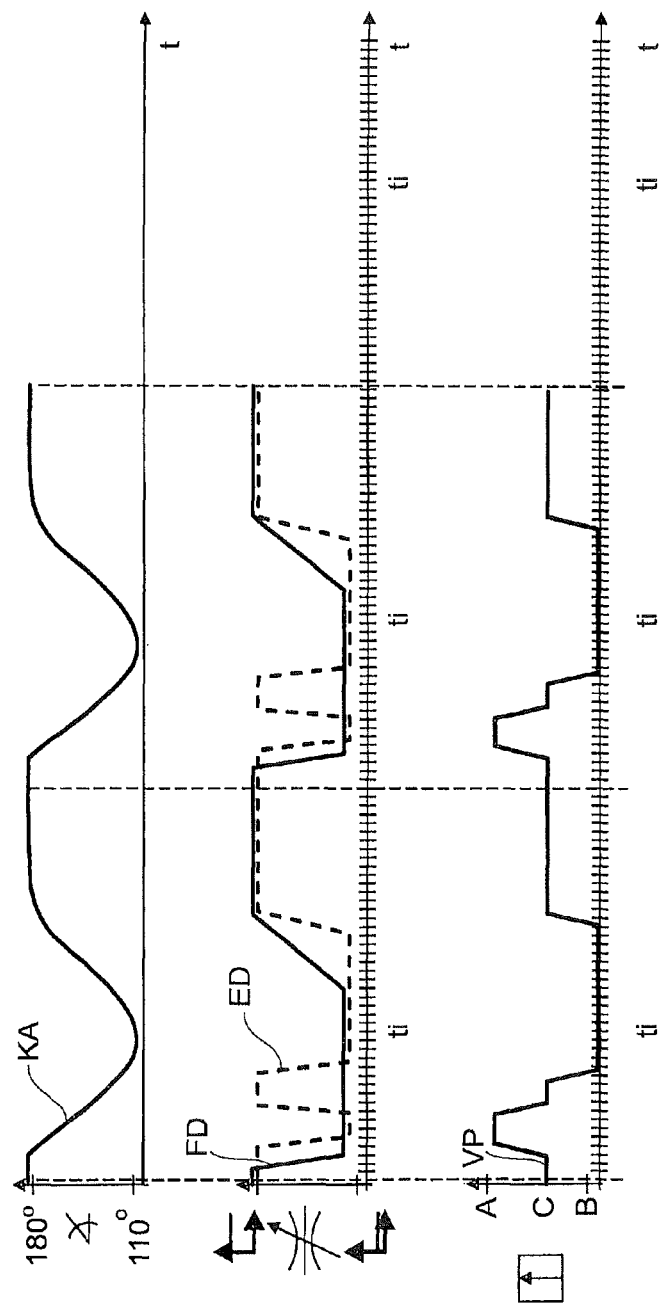
FIG. 5 shows a timing diagram for going up stairs.

In FIG. 5, the diagrams for going up stairs are recorded. There is no ankle moment. After the raising of the foot, the knee angle KA is reduced. In order to facilitate this, the extension damping ED is reduced; the switching device 60 moves into the position A, in order to bring about flexion assistance. The flexion damping FD continues to remain low. The extension damping ED is likewise reduced for the time period of the active flexion. Subsequently, the switching device 60 is moved into the position C, in order to achieve passive flexion with deceleration of the flexion movement, until the knee angle KA is minimal. Finally, the switching device 60 is moved into the valve position B, by which active extension is achieved, so that the assistance by the pressure providing device 20 can be made active. For the duration of the switching of the switching device 60, the extension damping ED is increased again; in the valve position B, in which active stretching is assisted, the extension damping ED is reduced, in order to ensure the full effectiveness of the assistance. The flexion damping FD is slowly increased, in dependence on the knee angle KA, during the raising of the patient, whereby the assisting moment becomes smaller and a hard strike against the extension limit stop is avoided. In addition, with an almost stretched-out knee joint, the extension damping ED is increased, in order likewise to dampen a hard strike.

Figure 5A:
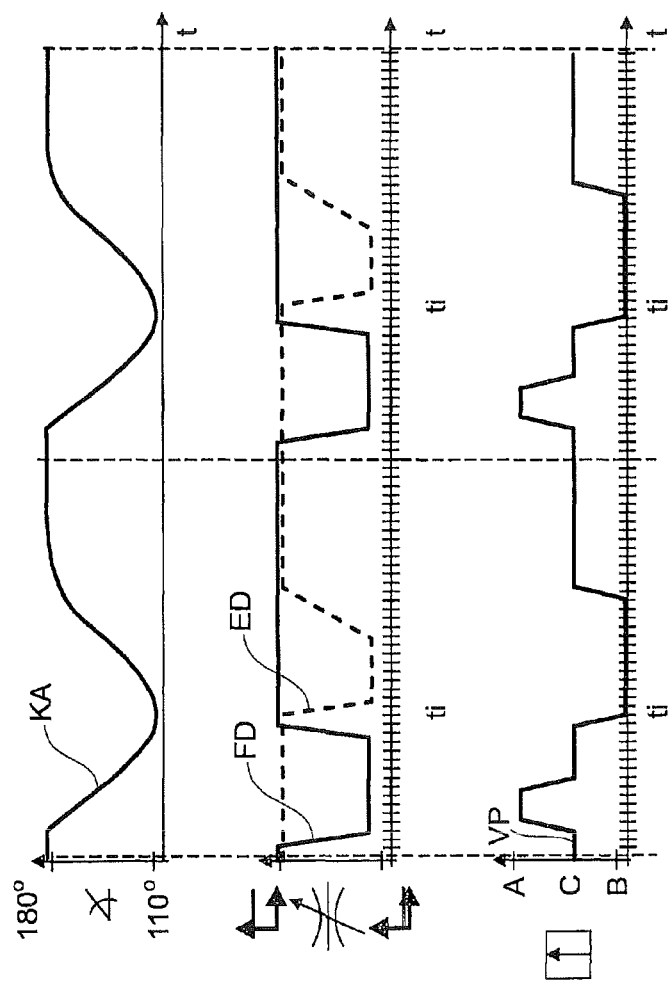
FIG. 5a shows a variant of the timing diagram for going up stairs.

In FIG. 5a, a variant of the timing diagram according to FIG. 5 is shown. The control device detects the situation that a step is to be climbed. Starting from the position C, as from a defined knee angle the switching device 60 is moved into the position A, in order to achieve active bending assistance. The patient is thereby provided with assistance in bending the prosthetic leg for the step, in order that the prosthetic foot can swing backward in order not to be caught on the lower edge of a step on stairs. In order to ensure the effectiveness of the active bending assistance, the flexion damping FD is reduced. The extension damping remains at the high starting level.

As from a defined target angle of the knee angle KA, the flexion assistance is switched off and the switching device 60 returns to the position C. The flexion damping FD and the extension damping ED remain unchanged. Shortly before reaching the maximum knee angle, the flexion damping is increased, in order to limit the maximum knee angle KA. After reaching the maximum flexion angle and the setting down of the foot, the extension assistance is activated and the switching device 60 is moved into the valve position B. At the same time, the extension damping ED is reduced, in order to ensure full assistance for the lifting movement. The flexion damping is left at a high level, for example in order to prevent the patient from falling back. When raising up the patient, the extension damping ED is slowly increased in dependence on the knee angle KA, in order to reduce the assisting moment by the pump 21 or the pressure accumulator 23 and avoid a hard abutment against the extension limit stop. After reaching the maximum stretching angle, the assistance is switched off and the valve position B is switched on.

Figure 6:
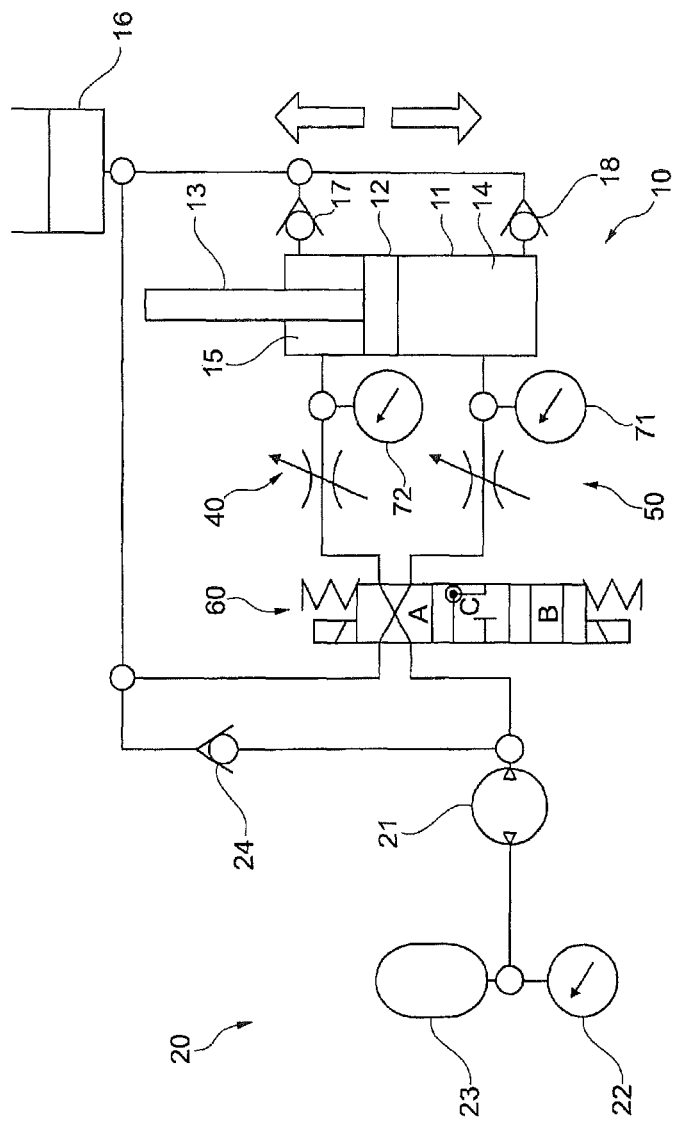
FIG. 6 shows a variant of the circuit arrangement.

In FIG. 6, a variant of the active flexion assistance is shown. The hydraulic unit 10 and also the switching device 60 correspond substantially to those of FIG. 2. The pressure providing device 20, however, is coupled to the other components in a different way. The pump 21 is designed as a pump that can deliver in both directions, so that the pressure accumulator 23 can also charge. The pressure accumulator 23 is connected to the pump 21 by a branch line. In this way it is possible that a separate admission of pressure to the pressure accumulator 23 is performed. If the pressure accumulator 23 is discharged, that is to say hydraulic fluid is delivered from the pressure accumulator 23 in the direction of the hydraulic unit 10, the pump 21 can additionally increase the pressure by the motor. In this case, it is possible to realize two different pressures, since flexion assistance generally requires less pressure than extension assistance. In addition, it is possible to use the pump 21 as a generator. If the pressure in the pressure accumulator 23 is much higher than is required within the hydraulic cylinder of the hydraulic unit 10, the pump 21 can be operated in a generator mode, in order to bring about a reduction in pressure and at the same time convert part of the hydraulic energy into electrical energy. The hydraulic energy would otherwise be lost at the respective valves 40, 50, since it is intended that the pressure is always switched on smoothly. By controlling the release of generator energy, it is possible to work with variable differences in pressure, whereby the lost power and the conversion of the pressure energy into heat can be minimized.

In addition, it is possible with the circuit according to FIG. 6 that the pressure in the accumulator 23 can be significantly increased without leading to increased losses at the valves 40, 50. The accumulator 23 can consequently store more energy from the movements of the joint device. When the hydraulic fluid is fed through from the pressure accumulator 23 to the hydraulic unit, the pump 21 can be operated in generator mode, in order to make an adaptation of the desired hydraulic pressure possible. The reduction of the pressure takes place by conversion into electrical energy, which can be stored and used for operating the pump 21. As long as no active assistance is necessary for the extension movement, this position of the control device 60 can also be used for admitting the hydraulic fluid to the pressure accumulator 23. For this purpose, the pressure in the pressure accumulator 23 is measured by way of the pressure sensor 22; at the same time, the pressure on the hydraulic cylinder 11 is measured at the outlet of the flexion chamber 15. The pressure sensor 72 indicates whether there is a difference in pressure between the pressure accumulator 23 and the flexion chamber 15. The flexion valve 40 is set in dependence on the difference in pressure. If there is no pressure in the pressure accumulator 23, the user of a prosthesis would not experience any resistance when the flexion valve 40 is opened completely and would fall. The flexion valve 40 is therefore switched in dependence on the pressures in such a way that the user of the joint device always feels the same resistance when going down stairs. Something similar applies when going down an incline on a slope. The pressure accumulator 23 charges further with every step down an incline, and pressure is thereby admitted to it.

As a further option, be provided, one pressures, accumulator may be provided, one that is designed for very high pressures, higher than those pressures that the pressure accumulator 23 requires for normal operation of the joint device. The additional accumulator can be charged to a very high level by going down an incline or going down stairs, so that the energy storage potential increases. There is the possibility that the pump 21 is thereby operated as a pneumatic motor, so that electrical energy can be generated in generator mode. The additional accumulator could also be discharged into the pressure accumulator 23 in a controlled manner, in order to create pressure reserves.

Figure 7:
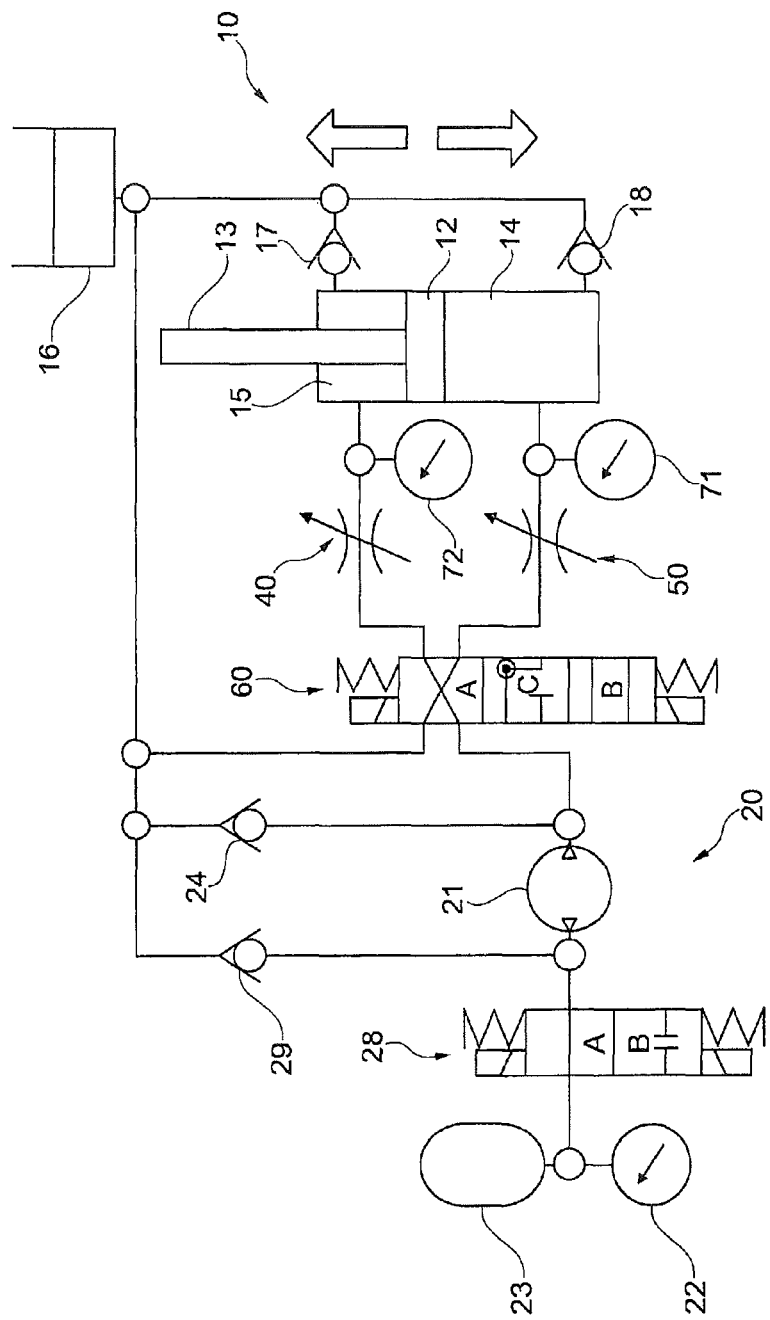
FIG. 7 shows a further variant of the circuit arrangement.

In FIG. 7, a variant of FIG. 6 is shown, a variant providing that between the pump 21 or the generator and the pressure accumulator 23 there is arranged a switching valve 28, with which it is possible to decouple the pressure accumulator 23 from the other components. As a result, it is possible to operate the pump 21 independently of the pressure accumulator 23. Provided for this purpose is a further check valve 29, which is arranged parallel to the already existing check valve 24. Both check valves 24, 29 prevent hydraulic fluid from being delivered from the pump 21 into the reservoir 16.

Figure 8:
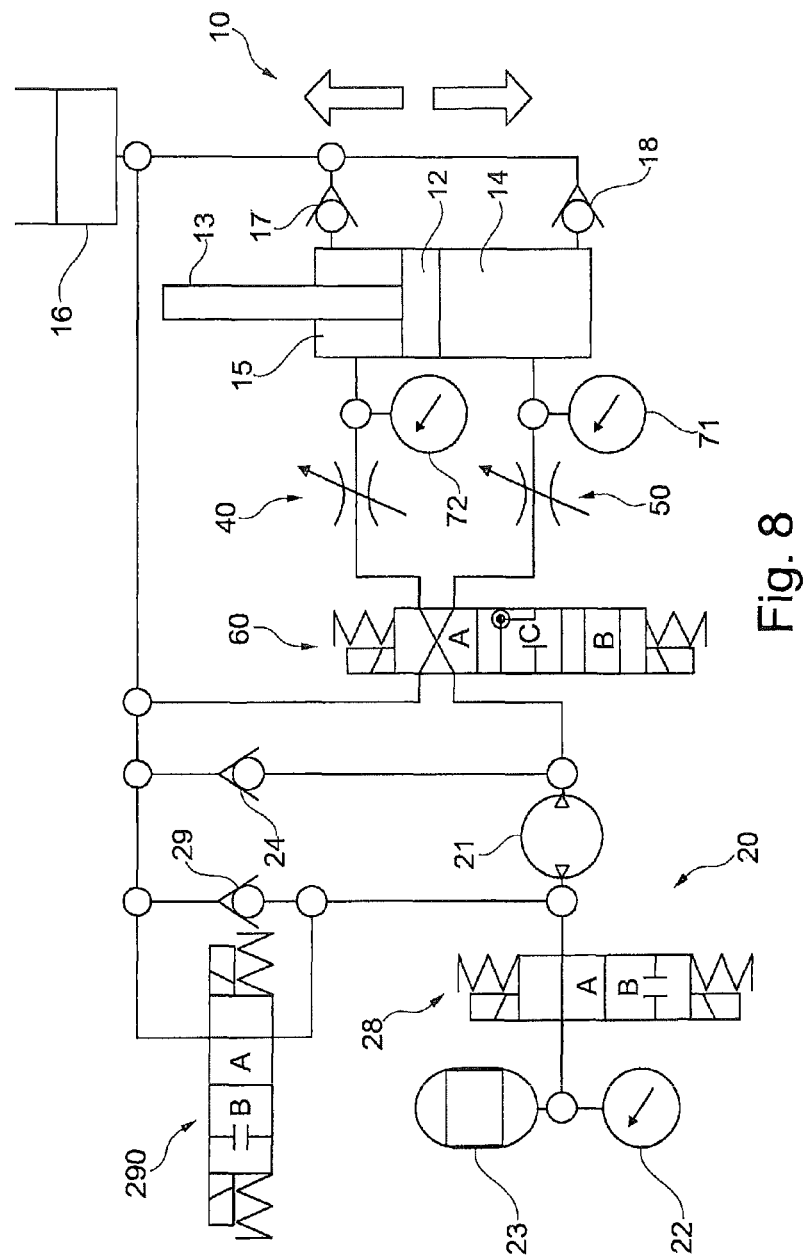
FIG. 8 shows a variant of the circuit arrangement as shown in FIG. 7.

In FIG. 8, a variant of the embodiment according to FIG. 7 is shown. The embodiment according to FIG. 8 provides that a switching valve device 290 is arranged parallel to the check valve 29 in the hydraulic line. This valve device 290 makes it possible to bypass the check valve 29 when it is in the switching position A. This switching position is shown. In the switching position B of the valve device 290, the bypass is shut off, so that hydraulic fluid cannot flow through the check valve 29 when there is a corresponding pressure gradient at the valve 29. This additional valve device 290 serves the purpose that, when there is a filled pressure accumulator 23, an oil flow enforced by a bending of the knee can be used for generating power by way of the pump 21 in a generator mode. For this purpose, the valve devices 290, 28, 60 should be moved into the corresponding positions, so that the pump 21 can be driven by the hydraulic fluid in generator mode during the flexion. The generator mode has the effect that possibly additional flexion damping is achieved by the conversion of the mechanical and hydraulic energy into electrical energy.

Figure 9:
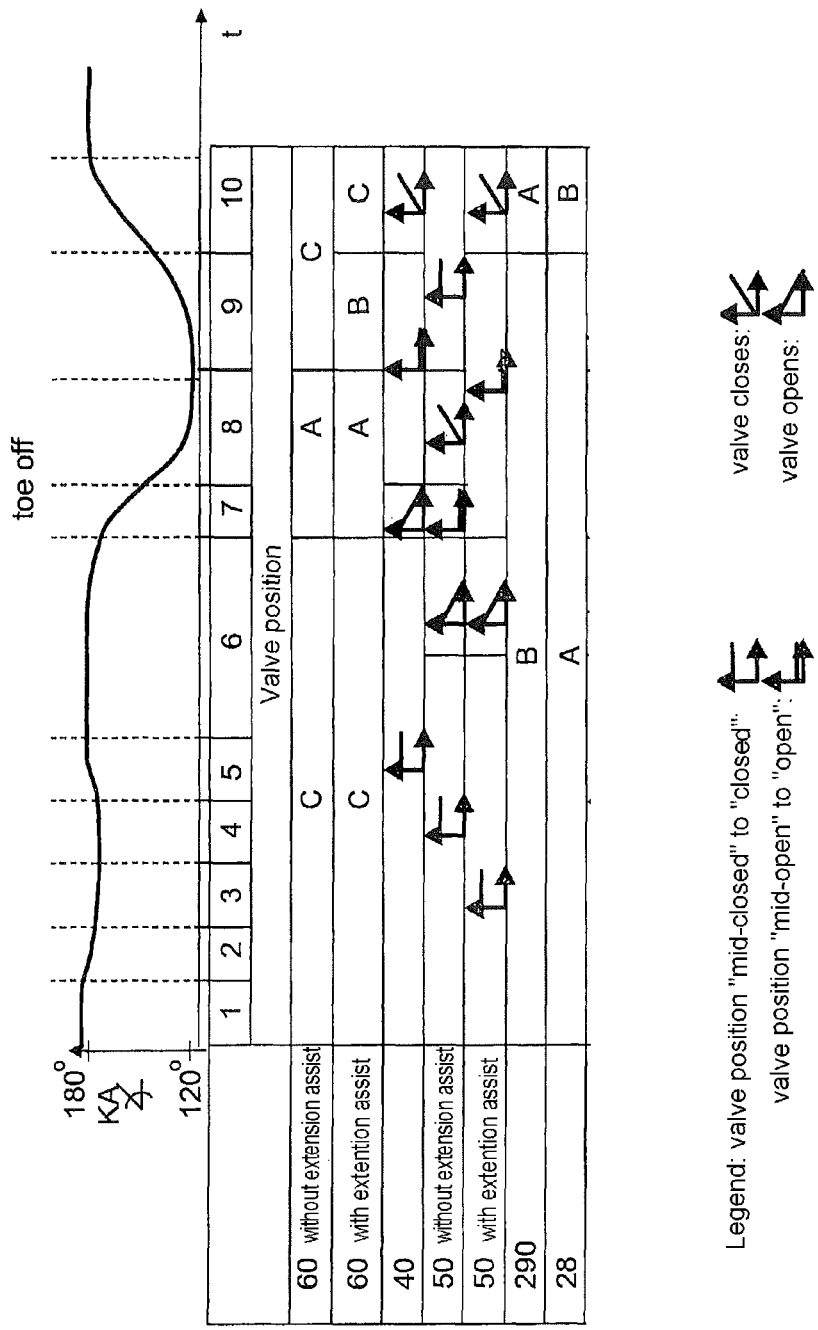
FIGS. 9 to 12 show control sequences for various walking situations.

In FIG. 9, the position of the individual valves or control devices and their changes over the progression of a step are shown in tabular form. Above the table, a step cycle for walking on the level is shown. The usual knee angle KA runs between approximately 180° in the maximum-stretched position and about 120° in the maximum-flexed position. A gait cycle can be divided into multiple phases, the most important division taking place between the standing phase and the swinging phase. Shown is the progression of the knee angle, beginning with the heel strike, that is to say the setting down of a prosthetic foot joint, which is followed by a standing phase flexion. After the first contact with the ground, in which the knee joint is in a stable position, the knee joint is bent by the loading due to the body weight. The flexion immediately following the loading damps the impulse due to the ground contact. The initial ground contact and the loading response take place in the time periods 1 to 4. Subsequently, an extension of the knee joint is initiated, in order to achieve improved stability.

Subsequently, the extension is completed. These are the mid and terminal standing phases in the sixth time period. There is subsequently a passive flexion of the knee joint, in what is known as the forward swinging phase 7. At the end of the forward swinging phase 7, what is known as the "toe off" takes place, that is to say the lifting of the foot off the ground, in order that the leg can swing forward. In the initial swinging phase, the maximum flexion is then subsequently reached; in the mid swinging phase 9, the swinging forward of the leg is reached and, in the terminal swinging phase, the extension of the knee joint is pursued, in order to reach the maximum knee angle and carry out the preparation for the standing phase.

In the table presented below this sequence of movements, the individual elements of the hydraulic circuit of the joint device are shown for the situation with active extension assistance and without active extension assistance. Up until the terminal standing 30 phase, the switching device 60 is arranged in the middle position C; for the terminal standing phase up to the maximum flexion, it is brought into the valve position A, in order to make assistance possible during the initiation of bending. After reaching the maximum flexion, without the extension-assisting function, that is to say extension assistance, assistance by a pressure accumulator 23 or the pump 21 is switched off again. In the case of extension assistance, after reaching the maximum flexion switching into the valve position B takes place, in order to achieve extension assistance.

The extension valve 40 remains predominantly closed during the standing phase. The extension valve only opens at the beginning of the terminal standing phase, remains substantially open during the entire flexion phase and the extension valve is only closed again during the terminal swinging phase, in order to avoid a hard strike against the extension limit stop. The high extension damping during the standing phase prevents a hard strike in the extension during the standing phase extension.

The flexion valve 50 is initially predominantly closed, in order to dampen standing phase bending. After the standing phase extension, the flexion damping is reduced, in order to make bending possible. Before the initiation of bending, the flexion damping is reduced to the maximum extent, since here the knee joint is kept up against the limit stop by the ground reaction forces. Without extension assistance, the flexion damping is increased in the swinging phase in order to avoid over-swinging of the prosthetic foot and what is known as "heel rising". The flexion damping remains at a high level to allow stumbling to be averted. The flexion valve with the extension-assisting function does not provide any increase in the damping during the flexion phase because "heel rising" does not have to be avoided here, since this is brought about by the activation of the extension assistance. The damping in the direction of flexion remains low for longer in comparison with the damping without an extension-assisting function in order to make extension assistance possible. Subsequently, the flexion damping is increased again, in order to allow stumbling to be averted.

For the variant according to FIG. 8 with the valves 290 and 28, it is provided that the valve 290 remains closed, in order not to undergo any losses during the assistance or charging of an accumulator. At the end of the terminal swinging phase, the valve can be opened, in order to pass the oil flow through the pump 21 in generator mode, and thereby convert the mechanical energy into electrical energy. The valve 28 is only closed during the terminal swinging phase, in order when there is a filled accumulator 23 to use an enforced oil flow for generating power by way of the generator mode of the pump 21.

Figure 10:
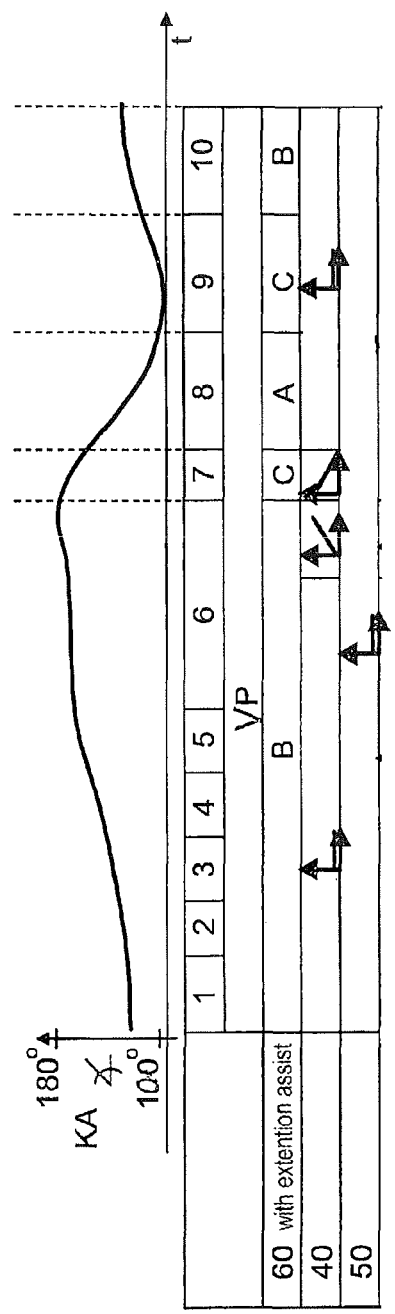

FIG. 10 shows the circuit arrangement when going steeply up an incline. It is advisable to work here with extension assistance. Up until the terminal standing phase, the valve 60 is in the position B, in order to ensure extension assistance, in order that the patient can climb a step of stairs more easily or can go up a sloping ramp more easily. Flexion assistance is provided in the initiation of bending after the toe off; extension assistance is provided in the terminal swinging phase. The extension valve 40 initially remains substantially open, in order to ensure low damping in the direction of extension, in order that the extension assistance is effective to the maximum extent. Before reaching the stretching limit stop, closing of the extension valve 40, and consequently increasing of the extension damping, is necessary in order to avoid a hard strike against the extension limit stop. At the switching times of the switching valve 60, brief closing of the extension valve may be appropriate in order to avoid hard impacts; alternatively, the flexion valve 50 may be briefly closed at these points in time. Otherwise, the flexion valve 50 is substantially open over the entire movement time period, in order to make minimal damping and maximum assistance possible.

Figure 11:
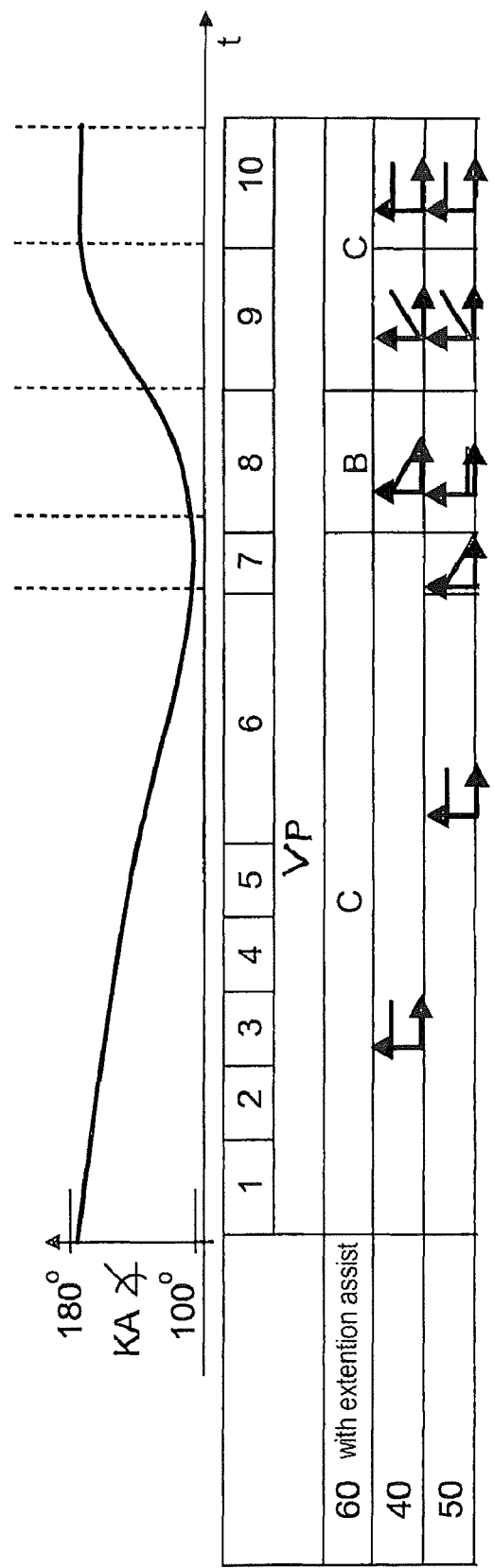

In FIG. 11, a diagram for going steeply down an incline with the extension-assisting function is shown. Over the entire standing phase, the switching valve remains in the position C; no extension assistance or flexion assistance takes place. Only in the initial swinging phase is the position B assumed, in order to achieve flexion assistance. The extension valve is closed in the standing phase, or has a high degree of damping, in order to ensure a high degree of extension damping when there is no longer a steep downward incline. After reaching the maximum flexion, the extension damping is reduced; in order to make the extension possible, the valve 40 is consequently opened. At the end of the swinging phase, the extension is increased again, in order to avoid hard striking against the extension limit stop.

The flexion valve 50 has increased flexion resistance during the standing phase, in order to dampen the bending during the downward movement. Subsequently, the flexion valve 50 is slowly opened, in order to make a flexion movement possible. In the swinging phase, the damping remains low, in order to make extension assistance possible, if so desired;

alternatively, the flexion damping may also be increased, as is provided in the region of the mid swinging phase. In the region of the terminal swinging phase, maximum flexion damping is again provided.

Figure 12:
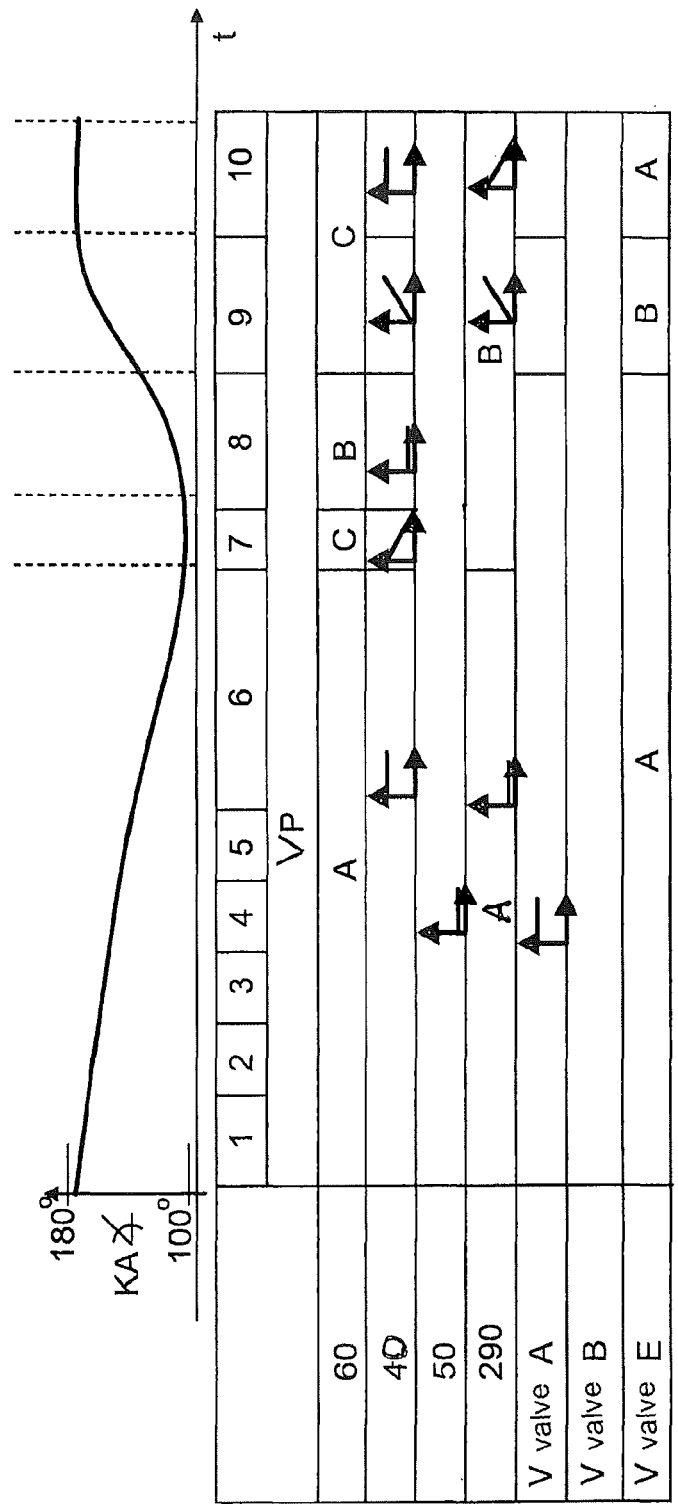

Shown in FIG. 12 are a circuit arrangement and a switching progression that can take place when steeply down an incline according to FIG. 11, if the pressure accumulator 23 is to be charged or if electrical energy is to be generated in the generator mode of the pump 21. The switching valve 60 is moved into the position A during the standing phase, in order that energy can be fed to the accumulator 23. It is advisable that this should only take place whenever the accumulator pressure does not exceed the piston pressure as a result. Should this be the case, the circuit diagram according to FIG. 11 would be applicable.

As a departure from FIG. 11, in the control according to FIG. 12 the extension valve is already opened in the terminal standing phase and the extension damping is reduced. The extension valve remains open over the entire initial swinging phase and is only closed again in the mid swinging phase, in order to increase the extension damping in order that a hard strike is avoided at the end of the swinging phase. The flexion valve remains open over the entire sequence of movements, in order to direct energy into the accumulator 23. The position of the valve should be adapted to the difference in pressure between the accumulator 23 and the piston. If the accumulator 23 is empty, the flexion valve 50 may be set in such a way that there is greater flexion damping. The flexion damping should likewise be kept low in the swinging phase, in order to make extension assistance possible, if so desired. The switching valve 290 is opened during the standing phase, in order that the oil flow through the generator can be used for obtaining power. The valve 28 remains closed. In the extension phase, the valve 290 is closed, in order that extension assistance by the pressure accumulator 23 can be made possible.

Figure 13:
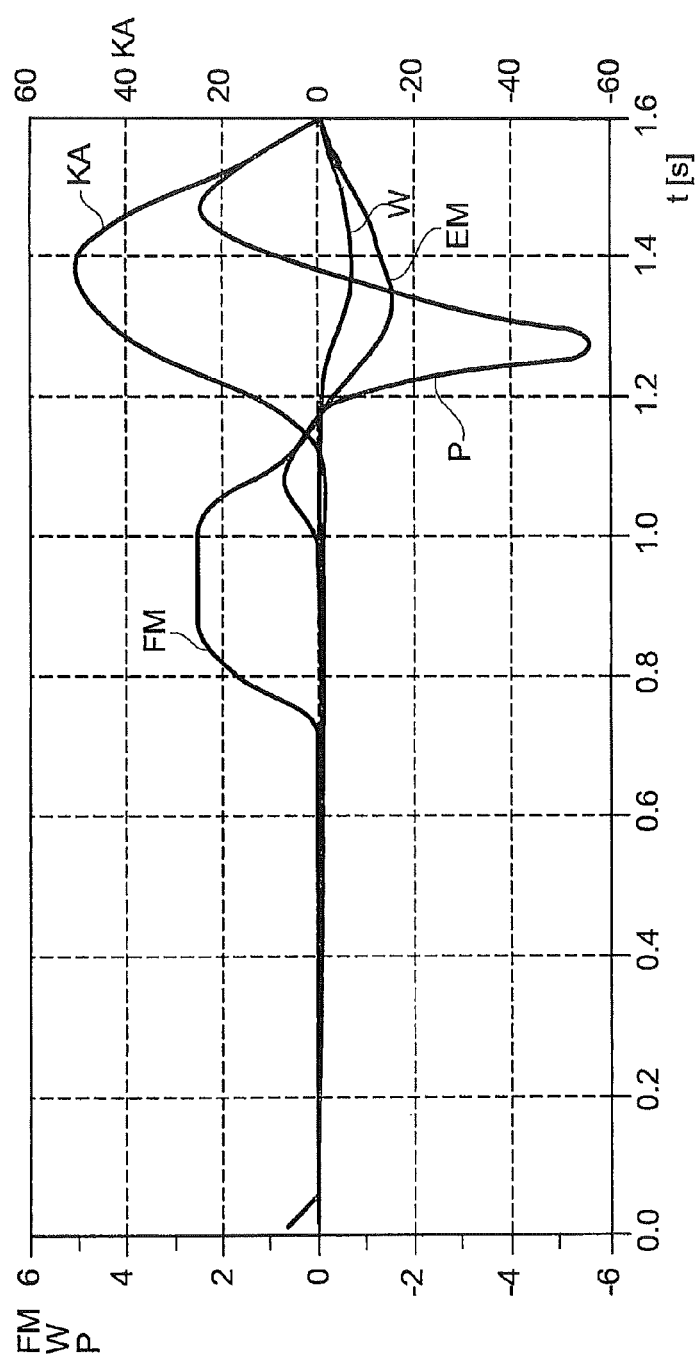
FIG. 13 shows a timing diagram for bending and stretching assistance.

Shown in FIG. 13 is a timing diagram for a gait cycle in which a knee angle KA is represented over time t. On account of the initial standing phase flexion, the knee angle KA is greater than 0° at the beginning of the gait cycle, that is to say when the heel touches down, known as the "heel strike"; it remains constant at 0° over the subsequent standing phase portion, until it increases after about 1.1 s. The knee angle KA increases further after the end of the standing phase, known as the "toe off", up to a maximum bending of about 55° at t=1.35 s. After reaching the maximum knee angle KA, a reversal of the movement takes place; the lower leg component is moved forward, so that the knee angle KA is reduced again on account of the extension movement, and at the end of the swinging phase, with the maximum or approximately maximum stretching, ends with a knee angle KA at 0°. As a departure from the representation in the other figures, the knee angle KA in FIG. 13 is denoted by 0° in the stretched position.

FIG. 13 also reveals that an assisting bending moment FM is applied immediately before the bending. It can be seen from the knee angle progression that the bending moment FM is not sufficient to bring about the bending of the knee; rather, the level of the bending moment FM is chosen such that only assistance for bending by the user is provided, and bending is not brought about independently. This is evident from the fact that the knee angle KA remains unchanged over the entire time period of the maximum bending moment FM. Already before the beginning of the bending, that is to say changing of the knee angle in the direction of the bending of the knee, the level of the bending moment FM is reduced, in order to avoid that the knee joint bends too easily, which would have inadequate stability of the knee joint as a consequence. The only temporary application of the bending moment has the advantage that less energy has to be provided. Likewise, the knee joint remains predominantly without bending assistance during the standing phase, so that increased security against unwanted bending is ensured. The assistance, which can be understood as reduction of the initiating moment for bending, allows a stable set-up to be chosen, so that an increased degree of standing stability can be provided, without this leading to an increased strain on the patient as a result of the secure set-up, that is to say the assignment of the individual components to one another.

After the "toe off", that is to say at about t=1.2 s, there is no longer an assisting bending moment; rather, an extension moment EM is applied, acting as flexion damping and preventing excessive bending of the knee joint. Instead of active application of an extension moment EM, purely passive damping may also take place; it is likewise possible that energy is drawn from the system by conversion for the damping, so that the energy required for the application of a bending moment can be at least partially returned. If a stretching moment EM is applied, the phase in which a stretching moment EM is applied is ended before complete stretching of the knee joint.

It is possible and intended that the energy remains applied even beyond the initiation of the movement, either at the same level or at a reduced level, in order to assist the user in the movement. The relatively low level of supplied energy prolongs the possible times of use without maintenance.

In the diagram according to FIG. 13, the applied power P and also the performed work W are also plotted. The power P supplied by motor increases at the beginning of the bending of the knee; after the "toe off", there is an excess of power, that is to say no motor power has to be supplied. After reaching the maximum knee angle, power is required again for extension, so that the power P becomes positive again.

Control such as that described on the basis of FIG. 13 can be carried out not only with a hydraulic drive device; it is similarly intended that the bending and stretching moments are applied directly by way of an electric motor, possibly with a suitable gear mechanism interposed. For damping the movement at the end, the motor may be changed over to generator mode, it being possible for the electrical energy generated to be stored in a storage battery or capacitor, in order to be able to call upon it at the appropriate time.

The invention claimed is:

1. A method for controlling an orthotic or prosthetic joint device with an upper part and a lower part arranged in an articulated manner thereon, fastening devices to secure the joint device on a user, a drive device to apply a moment to the orthotic or prosthetic joint device, and a control device communicatively coupled to at least one sensor and configured to control the drive device, the method comprising:
    applying a supporting moment to the orthotic or prosthetic joint device with the drive device during operation of the orthotic or prosthetic joint device when mounted to the user,
    the supporting moment being a flexion moment or an extension moment,
    the supporting moment being sufficient to support of an amount that supports a flexion movement or an extension movement and that is applied in the same direction as a flexion movement or an extension movement, respectively, of the lower part relative to the upper part, but that is less than an activation amount that causes the flexion movement or the extension movement, respectively, of the lower part relative to the upper part to reduce an amount of force required by the user to carry out the flexion movement or the extension movement;
    wherein only one of the supporting moments is applied at a time,
    wherein applying the supporting moment to the orthotic or prosthetic joint device includes applying the supporting moment as a flexion moment, in a time period before a swing phase flexion movement during a gait cycle,
    the gait cycle including an interval between two reoccurring heel strikes during walking;
    applying an activation moment to the orthotic or prosthetic joint device in the swing phase during the gait cycle, wherein the activation moment causes flexion movement or extension movement of the lower part relative to the upper part.

2. The method as claimed in claim 1, wherein applying the supporting moment to the orthotic or prosthetic joint device includes applying the supporting moment as a flexion moment, prior to the orthotic or prosthetic joint device being flexed and reducing the supporting moment when the orthotic or prosthetic joint device begins to flex.

3. The method as claimed in claim 1, wherein applying the supporting moment to the orthotic or prosthetic joint device includes applying the supporting moment as a flexion moment in a varying degree in dependence on a walking situation, the walking situation including walking on level ground, walking up an incline, or walking up stairs.

4. The method as claimed in claim 1, wherein applying the supporting moment to the orthotic or prosthetic joint device includes applying the supporting moment as a flexion moment including a first flexion moment that is applied after activation of the flexion movement of the lower part relative to the upper part, and a second flexion moment that is greater than the first flexion moment and is applied before activation of the flexion movement of the lower part relative to the upper part.

5. The method as claimed in claim 1, wherein applying the supporting moment to the orthotic or prosthetic joint device includes applying the supporting moment as a flexion moment, during the flexion movement up to a predetermined, ascertained flexion angle of the lower part relative to the upper part.

6. A method for controlling an orthotic or prosthetic joint device, comprising:
   providing the orthotic or prosthetic joint device having an upper part, a lower part rotatably connected to the upper part, a drive device to apply a flexion moment or an extension moment to the orthotic or prosthetic joint device, and a control device communicatively coupled to at least one sensor and configured to control the drive device;
   applying the flexion moment or the extension moment as a supporting moment to the orthotic or prosthetic joint device with the drive device during operation of the orthotic or prosthetic joint device when mounted to a user,
   the supporting moment being applied in the same direction as a flexion movement or an extension movement, respectively, of the lower part relative to the upper part, and being less than an activation amount that causes the flexion movement or the extension movement, respectively, of the lower part relative to the upper part to reduce an amount of a force required from the user to carry out the flexion movement or the extension movement;
   wherein only one of the flexion moment or the extension moment is applied at a time; and
   wherein applying the supporting moment as a flexion moment or an extension moment to the orthotic or prosthetic joint device includes applying in a time period before a swing phase flexion movement during a gait cycle, the gait cycle including an interval between two reoccurring heel strikes during walking;
   applying the flexion moment or the extension moment as an activation flexion moment or activation extension moment to the orthotic or prosthetic joint device with the drive device during operation of the orthotic or prosthetic joint device when mounted to a user in the swing phase during the gait cycle, the activation moment causing flexion movement or extension movement of the lower part relative to the upper part.

7. The method as claimed in claim 6, wherein applying the supporting moment to the orthotic or prosthetic joint device includes applying the supporting moment as a flexion moment, prior to the orthotic or prosthetic joint device being flexed and reducing the supporting moment when the orthotic or prosthetic joint device begins to flex.

8. The method as claimed in claim 6, wherein applying the supporting moment to the orthotic or prosthetic joint device includes applying the supporting moment as a flexion moment in a varying degree in dependence on a walking situation, the walking situation including walking on level ground, walking up an incline, or walking up stairs.

9. The method as claimed in claim 6, wherein applying the supporting moment to the orthotic or prosthetic joint device includes applying the supporting moment as a flexion moment including a first flexion moment that is applied after activation of the flexion movement of the lower part relative to the upper part, and a second flexion moment that is greater than the first flexion moment and is applied before activation of the flexion movement of the lower part relative to the upper part.

10. The method as claimed in claim 6, wherein applying the supporting moment to the orthotic or prosthetic joint device includes applying the supporting moment as a flexion moment during the flexion movement up to a predetermined, ascertained flexion angle of the lower part relative to the upper part.

11. A method for controlling an orthotic or prosthetic joint device, comprising:
   providing the orthotic or prosthetic joint device having an upper part, a lower part rotatably connected to the upper part, a drive device to apply a flexion moment or an extension moment to the orthotic or prosthetic joint device, and a control device communicatively coupled to at least one sensor and configured to control the drive device;
   applying the flexion moment or the extension moment as a supporting moment to the orthotic or prosthetic joint device with the drive device during operation of the orthotic or prosthetic joint device when mounted to a user,
   the supporting moment being applied in the same direction as the flexion movement or the extension movement, respectively, of the lower part relative to the upper part, and being less than an activation amount that causes the flexion movement or the extension movement, respectively, of the lower part relative to the upper part to reduce an amount of force required from the user to carry out the flexion movement or the extension movement;
   wherein only one of the flexion moment or the extension moment is applied at a time; and
   wherein applying the supporting moment as a flexion moment or an extension moment to the orthotic or prosthetic joint device includes applying the flexion moment in a time period before a swing phase extension movement during a gait cycle, the gait cycle including an interval between two reoccurring heel strikes during walking;
   applying the flexion moment or the extension moment as an activation flexion moment or activation extension moment to the orthotic or prosthetic joint device with the drive device during operation of the orthotic or prosthetic joint device when mounted to a user in the swing phase during the gait cycle, the activation moment causes flexion movement or extension movement of the lower part relative to the upper part.

12. The method as claimed in claim 11, wherein applying the supporting moment to the orthotic or prosthetic joint device includes applying the supporting moment as a flexion moment prior to the orthotic or prosthetic joint device being flexed and reducing the supporting moment when the orthotic or prosthetic joint device begins to flex.

13. The method as claimed in claim 11, wherein applying the supporting moment to the orthotic or prosthetic joint device includes applying the supporting moment as a flexion moment in a varying degree in dependence on a walking situation, the walking situation including walking on level ground, walking up an incline, or walking up stairs.

14. The method as claimed in claim 11, wherein applying the supporting moment to the orthotic or prosthetic joint device includes applying the supporting moment as a flexion moment including a first flexion moment that is applied after activation of the flexion movement of the lower part relative to the upper part, and a second flexion moment that is greater than the first flexion moment and is applied before activation of the flexion movement of the lower part relative to the upper part.

15. The method as claimed in claim 11, wherein applying the supporting moment to the orthotic or prosthetic joint device includes applying the supporting moment as a flexion moment during the flexion movement up to a predetermined, ascertained flexion angle of the lower part relative to the upper part.

16. A method for controlling an orthotic or prosthetic joint device with an upper part and a lower part arranged in an articulated manner thereon, fastening devices to secure the orthotic or prosthetic joint device on a user, a drive device to apply a moment to the orthotic or prosthetic joint device, and a control device communicatively coupled to at least one sensor and configured to control the drive device, the method comprising:

applying a supporting moment to the orthotic or prosthetic joint device with the drive device during operation of the orthotic or prosthetic joint device when mounted to the user, the supporting moment being a flexion moment or an extension moment, the supporting moments moment being sufficient to support a flexion movement or an extension movement and that is applied in the same direction as the flexion movement or the extension movement, respectively, of the lower part relative to the upper part, but that is less than an activation amount that causes the flexion movement or the extension movement, respectively, of the lower part relative to the upper part to reduce an amount of force required by the user to carry out the flexion movement or the extension movement;

wherein only one of the flexion moment or the extension moment is applied at a time, wherein applying the supporting moment to the orthotic or prosthetic joint device includes applying the supporting moment as a flexion moment, the supporting moment as an extension moment being applied in a time period before a swing phase extension movement during a gait cycle, the gait cycle including an interval between two reoccurring heel strikes during walking;

applying an activation moment to the orthotic or prosthetic joint device in the swing phase during the gait cycle, the activation moment causes the flexion movement or the extension movement of the lower part relative to the upper part.

17. The method as claimed in claim 16, wherein applying the supporting moment to the orthotic or prosthetic joint device includes applying the supporting moment as a flexion moment prior to the orthotic or prosthetic joint device being flexed and reducing the supporting moment when the orthotic or prosthetic joint device begins to flex.

18. The method as claimed in claim 16, wherein applying the supporting moment to the orthotic or prosthetic joint device includes applying the supporting moment as a flexion moment in a varying degree in dependence on a walking situation, the walking situation including walking on level ground, walking up an incline, or walking up stairs.

19. The method as claimed in claim 16, wherein applying the supporting moment to the orthotic or prosthetic joint device includes applying the supporting moment as a flexion moment including a first flexion moment that is applied after activation of the flexion movement of the lower part relative to the upper part, and a second flexion moment that is greater than the first flexion moment and is applied before activation of the flexion movement of the lower part relative to the upper part.

20. The method as claimed in claim 16, wherein applying the supporting moment to the orthotic or prosthetic joint device includes applying the supporting moment as a flexion moment during supporting the flexion movement up to a predetermined, ascertained flexion angle of the lower part relative to the upper part.

\* \* \* \* \*